(12) United States Patent
Hammami et al.

(10) Patent No.: US 11,260,352 B2
(45) Date of Patent: Mar. 1, 2022

(54) PERIODIC MESOPOROUS ORGANOSILICA-DOPED NANOCOMPOSITE MEMBRANES AND SYSTEMS INCLUDING SAME

(71) Applicant: KING ABDULLAH UNIVERSITY OF SCIENCE AND TECHNOLOGY, Thuwal (SA)

(72) Inventors: Mohamed Amen Hammami, Thuwal (SA); Lijo Francis, Thuwal (SA); Jonas Croissant, Thuwal (SA); Noreddine Ghaffour, Thuwal (SA); Shahad Alsaiari, Thuwal (SA); Niveen M. Khashab, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 375 days.

(21) Appl. No.: 16/311,080

(22) PCT Filed: Jun. 7, 2017

(86) PCT No.: PCT/IB2017/053366
§ 371 (c)(1),
(2) Date: Dec. 18, 2018

(87) PCT Pub. No.: WO2017/221094
PCT Pub. Date: Dec. 28, 2017

(65) Prior Publication Data
US 2020/0306701 A1    Oct. 1, 2020

Related U.S. Application Data

(60) Provisional application No. 62/352,316, filed on Jun. 20, 2016.

(51) Int. Cl.
B01D 71/64    (2006.01)
B01D 71/70    (2006.01)
(Continued)

(52) U.S. Cl.
CPC ............. *B01D 71/70* (2013.01); *B01D 69/14* (2013.01); *B01D 71/64* (2013.01); *B01D 61/364* (2013.01);
(Continued)

(58) Field of Classification Search
CPC ........ B01D 71/70; B01D 69/14; B01D 71/64; B01D 61/364; B01D 67/0004;
(Continued)

(56) References Cited

U.S. PATENT DOCUMENTS 8,029,671 B2    10/2011  Cath
2013/0206694 A1  8/2013  Nunes
(Continued)

FOREIGN PATENT DOCUMENTS

EP    2626127       8/2013
WO    2011117443    9/2011
WO    2015084266    6/2015

OTHER PUBLICATIONS

Zhiqiang Xu et al, Hydrophobization of Carbon-Supported Catalysts with 2,3,4,5,6-Pentafluorophenyl Moieties for Fuel Cells, Electrochemical and Solid-State Letters, 8 (10) A492-A494 (2005). (Year: 2005).*

(Continued)

*Primary Examiner* — Pranav N Patel
(74) *Attorney, Agent, or Firm* — Pabst Patent Group LLP

(57) ABSTRACT

A periodic mesoporous organosilica (PMO) nanoparticle functionalized nanocomposite membrane (NCM) for membrane distillation, the NCM including: polymer fibers such as polyetherimide fibers aggregated into a matrix; and
(Continued)

hydrophobic PMO nanoparticles disposed on the polymer fibers. The PMO nanoparticles include a framework connected by organic groups and pentafluorophenyl groups. Good membrane flux and anti-fouling was demonstrated. Membranes can be prepared by electrospinning.

11 Claims, 10 Drawing Sheets

(51) Int. Cl.
    *B01D 69/14*     (2006.01)
    *B01D 61/36*     (2006.01)
    *B01D 67/00*     (2006.01)
    *B82Y 30/00*     (2011.01)
    *B82Y 40/00*     (2011.01)

(52) U.S. Cl.
CPC ...... B01D 67/0004 (2013.01); B01D 67/0079 (2013.01); B01D 67/0093 (2013.01); B01D 2323/39 (2013.01); B82Y 30/00 (2013.01); B82Y 40/00 (2013.01)

(58) Field of Classification Search
CPC ............ B01D 67/0079; B01D 67/0093; B01D 2323/39; B01D 69/148; B82Y 30/00; B82Y 40/00
See application file for complete search history.

(56) References Cited

U.S. PATENT DOCUMENTS

2014/0158610 A1   6/2014  Qtaishat
2015/0053611 A1   2/2015  Wang

OTHER PUBLICATIONS

Jonas G. Croissant et al, Syntheses and applications of periodic mesoporous organosilica nanoparticles, Nanoscale, 2015, 7, 20318-20334. (Year: 2015).*
Chua, et al., "Mesoporous organosilica membranes: Effects of pore geometry and calcination conditions on the membrane distillation performance for desalination", Desalination, 370:53-62 (2015).
Croissant, et al., "Biodegradable ethylene-bis (propyl)disulfide-based periodic mesoporous organosilica nanorods and nanospheres for efficient in-vitro drug delivery", Advanced Materials, 26(35):6174-6180 (2014).
Croissant, et al., "One-pot Construction of Multipodal Hybrid Periodic Mesoporous Organosilica Nanoparticles with Crystal-Like Architechtures", Advanced Materials, 27:145-149 (2015b).
Croissant, et al., "Syntheses and Applications of Periodic Mesoporous Organosilica Nanoparticles", Nanoscale, 7:20318-20334 (2015a).
Dong, et al., "Superhydrophilic modification of PVDF-SiO2 electrospun nanofiber membranes for vaccuum membrane distillation", RSC Advances (2015).
Francis, et al., "PVDF hollow fiber abd nanofiber membranes for fresh water reclamation using membrane distillation", Journal of Materials Science, 49(5):2045-2053 (2014b).
Francis, et al., Fabrication and Characterization of functionally graded poly (vinylide fluoride)-silver nanocomposite hollow fibers for sustainable water recovery, Science of Advanced Materials, 6(12):2659-2665 (2014a).
Francis, et al., "Fabrication of electrospun nanofibrous membranes for membrane distillation application", Desalination and Water Treatment, 51(7-9):1337-1343 (2013).
Ghaffour, et al., "Technical review and evaluation of the economics of water desalination: current and future challenges for better water supply sustainability", Desalination, 309:197-207 (2013).
Guo, et al., "Desalination by Membrane Distillation using eelctrospun Polyamide Fiber Membranes with Surface Fluorination by Chemical Vapor Deposition", ACS applied materials & interfaces, 7(15):8225-8232 (2015).
Ho, et al., "Theoretical and Experimental studies of flux enhancement with roughened surface in direct contact membrane distillation desalination" Journal of Membrane Science, 433(0):160-166 (2013).
International Search Report PCT/IB2017/053366 dated Aug. 3, 2017.
Khayet, et al., Experimental design and optimization of asymmetric flat-sheet membranes prepared for direct contact membrane distillation, Journal of Membrane Science, 351(1):234-245 (2010).
Li, et al., "Electrospun Superhydrophobic Organic/Inorganic Composite Nanofibrous Membranes for Membrane Distillation", ACS Applied Materials & Interfaces, 7:21919-21930 (2015).
Ma, et al., Decorated electrospun fibers exhibiting superhydrophobicity, Advanced Materials, 19(2):255-259 (2007).
Munaweera, et al., "Novel wrinkled periodic mesoporous organsilica nanoparticles for hydrophobic anticancer drug delivery", Journal of Porous Material, 22(1):1-10 (2014).
UNICEF, World Health Organization, "Process on Drinking-Water and Sanitation-2012 Update", (2012).
Prince, et al., "Nanofiber based triple layer hydro-philic/-phobic membrane-a-solution for pore wetting in membrane distillation", Scientific reports, 4 (2014).
Tijing, et al., "A novel dual-layer bicomponent electrospun nanofibrous membrane for desalination by direct contact membrane distillation", Chemical Engineering Journal, 256:155-159 (2014b).
Tijing, et al., Recent progress of membrane distillation using electrospun nanofibrous membrane, Journal of Membrane Science, 453:435-462 (2014a).
Ving, et al. "Recent Advances in Functionalization of Mesoporous Silica", Journal of Nanoscience and Nanotechno., American Scientific Publishers, 5(3): 347-371 (2005).
Wang, et al., "Recent advances in membrane distillation processes: Membrane development, configuration design and application exploring", Journal of Membrane Science, 474:39-56 (2015).
Zhang, et al., "Fabrication of novel polyethermide-fluorinated silica organic-inorganic composite hollow fiber membranes intended for membrane contactor application", Journal of Membrane Science, 443170-190 (2013).
Lim, et al., "Synthesis of Ordered Microporous Silicates with Organosulfur Surface Groups and Their Applications as Solid Acid Catalysts", Chemistry of Materials, American Chemical Society, 10:2, 467-470 (1998).

* cited by examiner

PEI-PMO  PEI-PMO loaded anti-microbial agent

PERIODIC MESOPOROUS ORGANOSILICA-DOPED NANOCOMPOSITE MEMBRANES AND SYSTEMS INCLUDING SAME

CROSS-REFERENCE TO RELATED APPLICATIONS

This application is a National Phase application under 35 U.S.C. 371 of PCT/IB2017/053366 filed Jun. 7, 2017 entitled "PERIODIC MESOPOROUS ORGANOSILICA-DOPED NANOCOMPOSITE MEMBRANES AND SYSTEMS INCLUDING SAME," which claims benefit of and priority to U.S. Provisional Application No. 62/352,316 filed Jun. 20, 2016, which are hereby incorporated by reference in their entirety.

BACKGROUND

The shortage of fresh water has become a major problem in many parts of the world. According to the world health organization (WHO), the lack of fresh water may affect up to 4 billion people by 2050. In order to address this problem, various studies have been conducted with regard to improving the conversion of sea water into fresh water for human consumption and irrigation. The growing importance of water desalination has encouraged renewed focus on existing technology for water desalination. Reverse Osmosis (RO) is a major and commonly used membrane-based technology for seawater desalination. However, this technology is limited to relatively modest salinity because the osmotic pressure that must be overcome in RO increases with the salt concentration in the feed stream. In addition, RO processes are generally energy intensive, have high investment costs, and may have a large footprint due to extensive pretreatment.

In view of the limitations encountered in the RO process, researchers sought methods that are easier to operate. One such technique is membrane distillation (MD). MD is a thermally driven process that can be an attractive alternative for water desalination. In an MD process having a direct contact configuration, feed and permeate streams may flow along opposing sides (e.g., a feed side and a permeate side) of a hydrophobic microporous membrane. Francis, L. et al., Fabrication of electrospun nanofibrous membranes for membrane distillation application. *Desalination and Water Treatment* 2013, 51 (7-9), 1337-1343.

Water vapor is transported from the feed to the permeate side due to a vapor pressure gradient across the membrane. MD desalination process may provide a high purity water product, without the need for external hydraulic pressure, and may be applied to high concentration salt solutions. However, one of the challenges facing the MD development is fabrication of suitable membranes with specific characteristics. Khayet, M., et al., Experimental design and optimization of asymmetric flat-sheet membranes prepared for direct contact membrane distillation. *Journal of Membrane Science* 2010, 351 (1), 234-245.

In the past few years, several studies have been reported in incorporating nanoparticles in electrospun nanofibers or in hollow fibers to impart functionalities to distillation membranes. For example, Francis and co-authors reported the use of hydrophobic silver nanoparticles to functionalize hollow poly vinylidene fluoride (PVDF) fibers. Francis, L., et al., Fabrication and Characterization of Functionally Graded Poly (vinylidene fluoride)—Silver Nanocomposite Hollow Fibers for Sustainable Water Recovery. *Science of Advanced Materials* 2014, 6 (12), 2659-2665. The incorporation of nanoparticles not only improved the hydrophobicity of the hollow fiber membrane but also improved the mechanical properties and the distillation performance of the membrane. In recent work, researchers have used surface modifying macromolecules (SMM) with hydrophilic or hydrophobic properties to make triple layer membranes having a highly hydrophobic feed side layer and a hydrophilic permeate side layer to prevent pore wetting and to improve distillation flux. Prince, J., et al., Nanofiber based triple layer hydro-philic/-phobic membrane-a solution for pore wetting in membrane distillation. *Scientific Reports* 2014, 4: 6949, 1-6. Organically-modified silica nanoparticles have been also used to impart functionalities to the fiber membranes as well. Xiong Li and co-authors studied the incorporation of different sizes of super hydrophobic silica nanoparticles in the PVDF nanofibers. In this paper, the composite nanofibers were asserted to have a higher flux and lifetime, as compared to pure PVDF nanofibers. Li, X., et al.; Electrospun Superhydrophobic Organic/Inorganic Composite Nanofibrous Membranes for Membrane Distillation. *ACS Applied Materials & Interfaces* 2015, 7, 21919-21930. In another paper, as a way to improve the hydrophobic properties of polyetherimide (PEI) hollow fiber membranes, authors used fluorinated silica nanoparticles. Zhang, Y.; et al., Fabrication of novel polyetherimide-fluorinated silica organic-inorganic composite hollow fiber membranes intended for membrane contactor application. *Journal of Membrane Science* 2013, 443, 170-180. The resulting nanocomposite membrane was applied a $CO_2$ separator gas-liquid membrane contactor system, and researchers claimed a stable performance for 31 days of long term operations. See also US Patent Publications 2015/0053611 and 2014/0158610.

However, the above membranes suffer from lower process performance. In addition, biofouling is a potential drawback of the membrane based desalination process, particularly when the membranes are used in real-world conditions.

Accordingly, there is a need for improved materials and membranes, particularly for use in MD processes and MD systems including the same. In particular, a need exists for better improving the anti-biofouling properties for MD.

SUMMARY

Aspects and embodiments described herein include compositions, devices, and articles, methods of making such compositions, devices, and articles, and methods of using such compositions, devices, and articles. The compositions can be, for example, particle or nanoparticle compositions.

A first aspect provides for a nanocomposite membrane (NCM) for membrane distillation, the NCM comprising: polymer fibers aggregated into a matrix; and periodic mesoporous organosilica (PMO) nanoparticles disposed on the polymer fibers, the PMO nanoparticles comprising hydrophobic functional groups.

A second aspect provides for a nanocomposite membrane (NCM) for membrane distillation, the NCM comprising: polyetherimide (PEI) fibers aggregated into a matrix; and periodic mesoporous organosilica (PMO) nanoparticles disposed on the PEI fibers.

In one embodiment, the hydrophobic functional groups comprise fluorinated organic groups.

In one embodiment, the fluorinated organic groups comprise pentafluorophenyl groups.

In one embodiment, the pentafluorophenyl groups are covalently bonded to silicon atoms of the PMO nanoparticles.

In one embodiment, wherein the PMO nanoparticles comprise —$CH_2CH_2$— bivalent groups.

In one embodiment, the polymer fibers comprise polyetherimide (PEI), poly vinylidene fluoride (PVDF), poly(methyl methacrylate (PMMA), polysulfone, or any combination thereof.

In one embodiment, the polymer fibers comprise polyetherimide (PEI).

A third aspect provides for a periodic mesoporous organosilica (PMO) nanoparticle composition comprising hydrophobic groups.

Methods of making the membranes and compositions are also provides. For example, the method of making the membrane comprises the step of electrospinning.

Methods of using the membranes are also provided including membrane distillation.

A variety of one or more advantages can flow from one or more embodiments described herein. These include, for example, unexpectedly high membrane fluxes, increased strength and durability, thermal stability, ability to tune hydrophobicity and hydrophilicity, environmental friendliness, low toxicity, anti-fouling and antiscaling properties, and/or lower cost. The high porosity can allow a membrane to be loaded with different cargo and functionalize the membrane with, for example, antimicrobial and/or antioxidant activity.

DETAILED DESCRIPTION

Introduction

All references cited herein are incorporated herein by reference. No admission is made that any reference cited or description provided herein is prior art. Additional description for the elements of the aspects and embodiments summarized above are provided below.

The terms "consisting essentially of" and "consisting of" are part of the present disclosure. For example, they may be used in place of terms such as "comprising" or "comprises." Basic and novel features of the present inventions are described and inherently provided herein.

Composite Nanofiber (Nanocomposite) Membrane (NCM)

According to various embodiments, provided is an NCM that includes polymeric fibers functionalized with periodic mesoporous organosilica (PMO) nanoparticles. The fibers may be microfibers and/or nanofibers and may be aggregated into a matrix. The matrix may form a feed (e.g., brine) contact surface of the NCM. The PMO nanoparticles may be disposed on surfaces of the fibers. For example, the PMO nanoparticles may be incorporated into surfaces of the fibers during the formation of the fibers or may be attached to or coated on previously formed fibers. The PMO nanoparticles may be attached to the fibers by, for example, electrostatic attraction or covalent bonding reaction.

Figure 10:
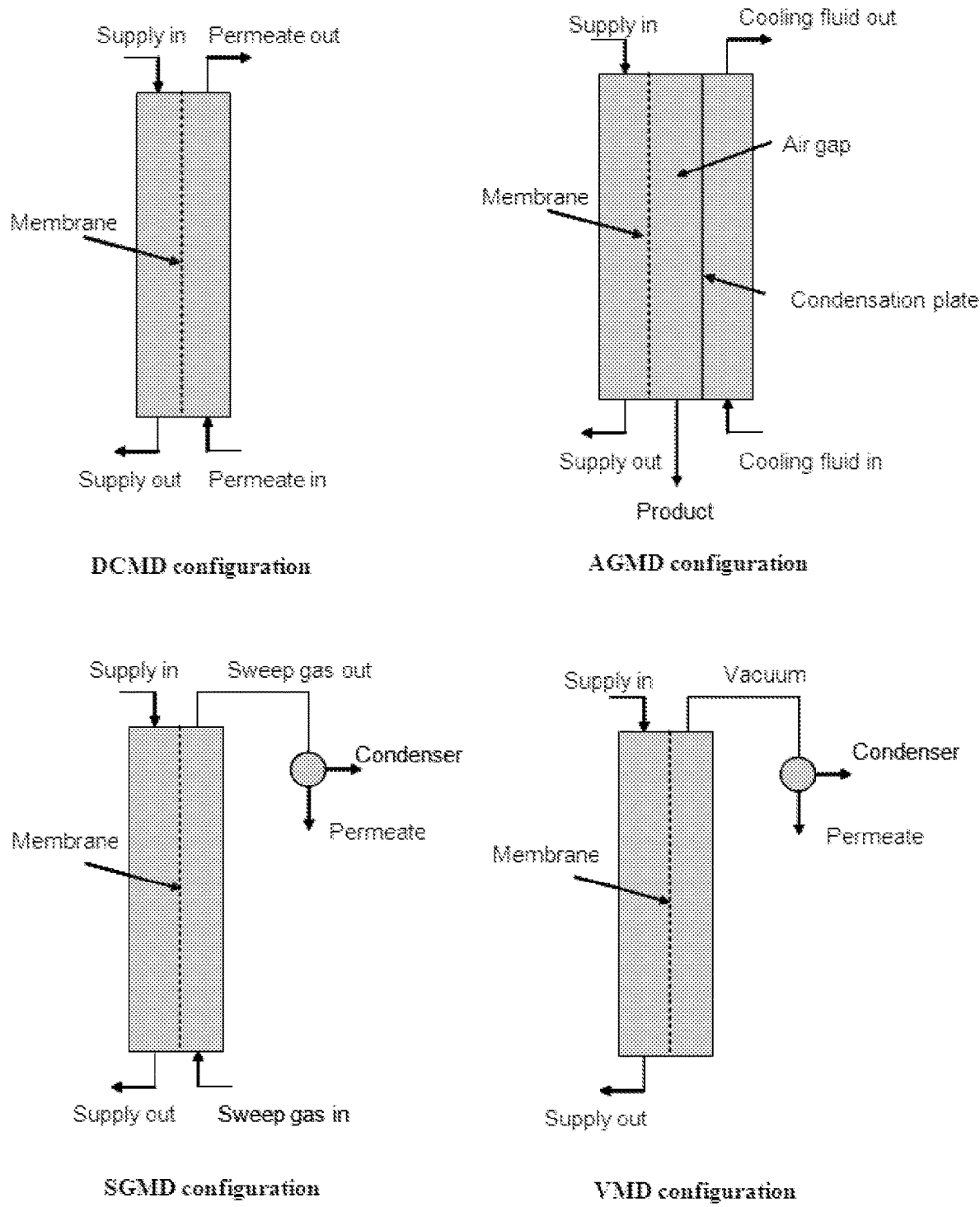
FIG. 10 illustrates four types of membrane distillation embodiments.

The membrane may be utilized in membrane distillation (MD) processes and/or systems. For example, the NCM may be included in a direct contact MD system (DCMD), an air gap MD system (AGMD), a sweep gas MD system (SGMD), and/or a vacuum MD system (VMD). See, FIG. 10, for example, for illustrations of these different embodiments. Other types of MD processes or systems can be used. See, for example, Tijing, L. D., et al., Recent progress of membrane distillation using electrospun nanofibrous membrane. *Journal of Membrane Science* 2014, 453, 435-462.

The properties of the NCM, such as the thickness and/or pore size thereof, may determined according to the characteristics of a distillation system including the NCM. For example, according to some embodiments, such as when the NCM is included in a MD system, the NCM may have a thickness ranging from about 30 microns to about 300 microns, or about 50 microns to about 200 microns, or about 50 microns to about 150 microns, and an average pore size ranging from about 0.1 microns to 1.5 microns. The NCM may also have a water contact angle of at least about 90°, or at least about 120°, or at least 130°, or at least 135°, or at least 140°, or less than about 170°, ranging from about 90° to about 170°. The contact angle can be less than 160°. Further, the NCM may have a flux ranging from about 20 $Kg/m^2h$ to about 200 $Kg/m^2h$.

According to some embodiments, the fibrous matrix of the NCM may be formed by electrospinning. See, for example, Tijing, L. D., et al., Recent progress of membrane distillation using electrospun nanofibrous membrane. *Journal of Membrane Science* 2014, 453, 435-462. The electrospinning technique also may be found in a paper by L. Francis et al. which is incorporated herein by reference (L. Francis et al., *Desalination and Water Treatment* 51 (2013) 1337-1342). However, according to some embodiments, the NCM may be a cast membrane, a hollow fiber membrane, or a phase-inversion flat sheet membrane, for example.

In one embodiment, the matrix is formed by electrospinning a mixture comprising the polymer such as polyetherimide (PEI), at least one solvent, and the PMO nanoparticles.

In one embodiment, the solvent comprises an aprotic organic solvent such as, for example, N-methyl-2-pyrrolidone (NMP).

In one embodiment, the mixture comprises: from about 5 to about 25 wt % PMO nanoparticles, based on 100 wt % of the polymer such as PEI; and from about 15 to about 25 wt % of the polymer such as PEI, based on 100 wt % of the solvent. In another embodiment, the mixture comprises:

from about 5 to about 20 wt % PMO nanoparticles, based on 100 wt % of the polymer such as PEI; and from about 15 to about 20 wt % of the polymer such as PEI, based on 100 wt % of the solvent According to various embodiments, the NCM may include a support configured to support the fibrous matrix. The support can be, for example, hydrophobic or hydrophilic. In one embodiment, a polymeric support such as a polyester non-woven support can be used.

PMO Nanoparticles

Periodic mesoporous organosilicas (PMOs) are known in the art including nanoparticles of PMOs. See, for example, Croissant et al., "Syntheses and Applications of Periodic Mesoporous Organosilica Nanoparticles," Nanoscale, 2015, 20318-20334; Croissant et al., *Advanced Materials*, 2015, 27, 145-149; Croissant et al., *Adv. Mater.*, 2014, DOI: 10.1002/adma.201401931; and references cited in these references. Mesoporous pores can be characterized as having diameters of about 2 nm to about 50 nm. In contrast, microporous pores can be less than 2 nm, and macroporous pores can be greater than about 50 nm.

As noted above, the NCM may include a polymer functionalized with PMO nanoparticles. The PMO nanoparticles may be generally spherical particles having an average diameter of from about, for example, 50 nm to about 500 nm, or about 100 nm to about 200 nm. However, according to some embodiments, the PMO nanoparticles may have other shapes and/or sizes. The PMO nanoparticles can be porous.

The PMO nanoparticles may include a framework of polysilsesquioxanes connected by organic bridging groups. For example, the bridged polysilsesquioxane can be generically represented by the formula $O_{1.5}Si—R—SiO_{1.5}$., where R represents the organic bridging group. They can be prepared from reactive bridged compounds $(R'O)_3Si—R—Si(OR')_3$, wherein R' can be a monovalent moiety such as alkyl and R can be a bivalent moiety such as alkylene as known in the art. R and R' can be, for example, C1-C6 moieties, or C2-C4 moieties. R can be, for example, $—CH_2CH_2—$. Each individual organic bridging group may be covalently bonded to two or more silicon atoms in the framework. The pores in the material can be periodically ordered with diameter in the range 2-50 nm, or 2-30 nm, or 2-10 nm, or 2-5 nm, or 2-3 nm. According to the type of bridging group, pores of the PMO nanoparticles may have various shapes, such as three-dimensional hexagonal ($P6_3$/mmc), cubic (Pm3n), two-dimensional hexagonal (P6mm), and wormlike, for example. Two or more reactive silane compounds can be used to create the PMO. For example, one silane compound can provide a hydrophobic or hydrophilic moiety.

The PMO nanoparticles may be functionalized with one or more modifying groups, in order to change one or more properties thereof. For example, the PMO nanoparticles may be functionalized with hydrophobic groups, in order to increase the hydrophobicity thereof. In particular, the PMO nanoparticles may be functionalized with fluorinated organic groups or non-fluorinated groups. For example, a pentafluorophenyl functional group may be covalently bonded to silane groups of the framework (e.g., covalently bonded to Si atoms of the framework). Examples of non-fluorinated groups include, for example, aminopropyl, mercaptopropyl, and dodecyl.

The PMO nanoparticles may be functionalized with other fluorinated groups, such as trifluoromethyl, heptadecafluorodecyl, 11-(pentafluorobenzyloxy)-undec-1-yl, and 11-(3,3,4,4,5,5,6,6,7,7,8,8,8-tridecafluoro-1-octyloxy)-undec-1-yl.

The hydrophobicity of the PMO nanoparticles may be tuned by controlling the amount and/or type of hydrophobic groups attached to the PMO nanoparticle framework. In various embodiments, the PMO nanoparticles may include from about 10 wt. % to about 40 wt % of the hydrophobic groups, based on the total weight of the PMO nanoparticles.

The PMO nanoparticles can be tested for zeta potential, and can be found to have negative surface characteristics. Hence, they can be attractive to positively charged groups in a polymer such as groups found in nitrogen-containing polymers such as polyethyleneimine, for example.

The PMO nanoparticles described herein can be used for a variety of applications which are not limited to membranes or membrane distillations. (J. G. Croissant et al., *Nanoscale* 7 (2015) 20318-20334)

NCM Polymer

According to various embodiments, the NCM may include a membrane-forming polymer. In particular, the polymer may be functionalized via doping with the PMO nanoparticles. Synthetic polymers useful for making membranes are known in the art. They can include, for example, imide repeat units or fluoro repeat units. Imide-containing polymers can be used such as, for example, PEI, PAI, PI, BTDA-TDI-MDI. The polymer may be any suitable membrane-forming polymer, such as polyetherimide (PEI), poly vinylidene fluoride (PVDF), poly(methyl methacrylate) (PMMA), polysulfone, or the like. The polymer may be in the form of hollow or solid microfibers or nanofibers, which may be electrospun and aggregated into a matrix to form the NCM. According to some embodiments, the fibers may have a diameter of about 50 nm to about 1,000 nm, or about 200 nm to about 600 nm. The fiber length is not particularly limited but can be adapted for the need.

The polymer may be hydrophobic in its native form, or may be functionalized to be hydrophobic or more hydrophobic.

The polymer may have a glass transition (Tg) temperature of less than 25° C. or greater than 25° C. The Tg can be, for example −50° C. to 10° C., or about −35° C. Alternatively, the polymer may have a Tg temperature of about or above about 100° C., or about or above about 150° C., or about or above about 200° C., such as from about 400 to about 450° C. It can be, for example, about 170° C.

The PMO nanoparticles may be regularly or irregularly dispersed along the polymer fibers. The polymer fibers may be doped with from about 2.5 to about 20 wt %, such as from about 5 to about 10 wt % of the PMO nanoparticles, with respect to the weight of the polymer fibers, when the doped polymer fibers are included in a NCM for a MD system.

The PMO nanoparticles may be attached to the polymer during electrospinning of the polymers to form the NCM. For example, Ma et al., which is incorporated herein by reference, discloses a suitable technique for doping electrospun particles with hydrophobic elements (Ma et al, *Adv. Mater.* 19 (2007), 255-259).

However, the PMO nanoparticles may be incorporated into any other kind of membranes used for water recovery processes, such as micro filtration (MF), ultrafiltration (UF), nanofiltration (NF), forward osmosis (FO), and reverse osmosis (RO) processes, in order to improve membrane and/or process performance. Such membranes may be fabricated by incorporating the PMO nanoparticles into different types of membranes such as electrospun nanofibrous membranes, phase inversion flat sheet membranes, or hollow fiber membranes.

MD System

Figure 1:
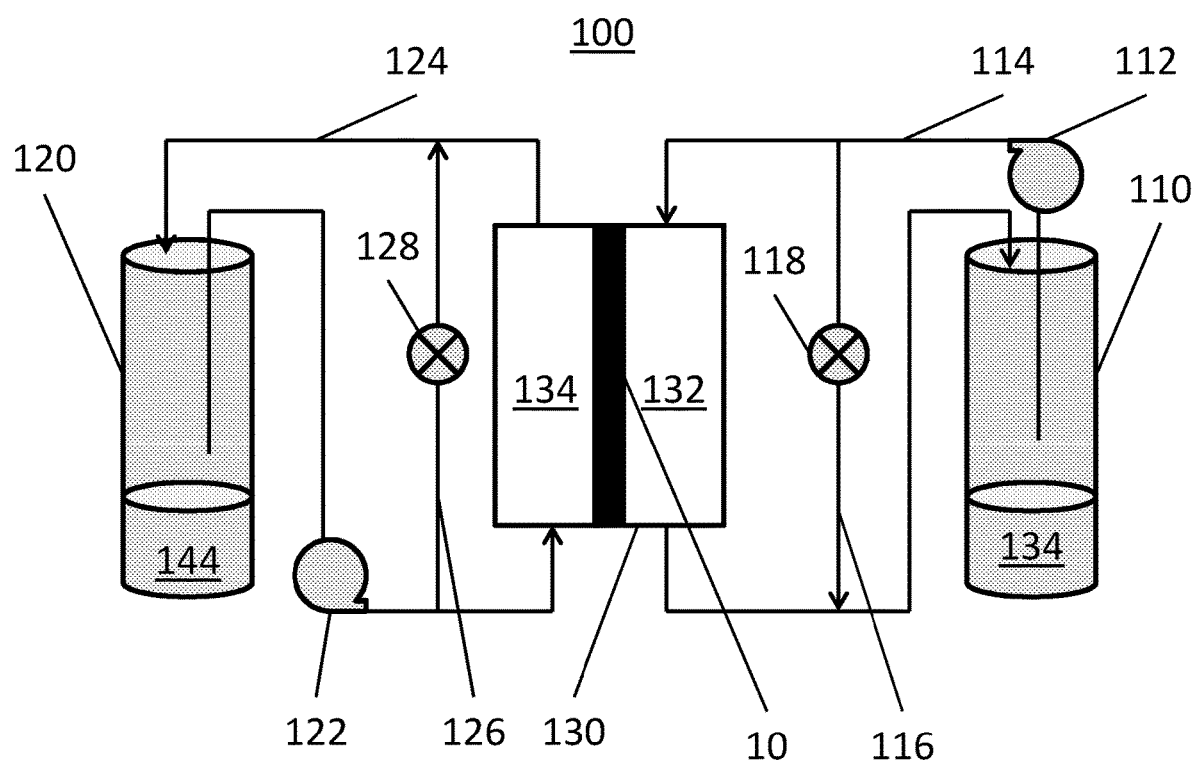
FIG. 1 is a schematic diagram for one embodiment of a membrane distillation system.

Membrane distillation is an important application for the membranes. FIG. 1 is a schematic diagram illustrating a direct contact MD system 100 including an NCM 10, according to various embodiments of the present disclosure. Referring to FIG. 1, the system 10 includes a feed vessel 110, a feed pump 112, a permeate vessel 120, a permeate pump 122, and a membrane module 130 including the NCM 10.

The feed pump 112 is configured to pump a feed fluid (e.g., brine) contained in the feed vessel 110, through a feed conduit 114 connecting the feed vessel 110 and the membrane module 130, such that the brine passes through a feed channel 132 of the membrane module 130. The permeate pump 112 is configured to pump a permeate fluid (e.g., fresh water) contained in the permeate vessel 120, through a permeate conduit 124 fluidly connecting the permeate vessel 130 and the membrane module 130, such that the fresh water passes through a permeate channel 134 of the cell 130.

The system 100 may also include a heater 134 configured to heat the brine in the feed vessel 110, and a chiller 144 configured to cool the fresh water in the permeate vessel 120. The system 100 may also include a feed bypass conduit 116 and a feed bypass valve 118, which are configured to allow at least some of the brine to bypass the membrane module 130. The system 100 may further include a permeate bypass conduit 126 and a permeate bypass valve 128, which are configured to allow at least some of the fresh water to bypass the membrane module 130.

Further, the system 100 may include various other elements, such as thermocouples, pressure gauges, flow meters, etc., in order to control fluid flow through the system.

In operation, a fresh water permeate is separated from the heated brine in the feed channel 132 by passing through the NCM 10. The permeate is then collected and/or condensed by the cool fresh water passing through the permeate channel 134 and collected in the permeate vessel 120. While the system 100 is shown to be a direct contact MD system, as would be apparent to one of ordinary skill in the art, the system 10 may also be configured as an air gap MD system, a sweep gas MD system, or a vacuum MD system, by altering the configuration of various components.

For example, the permeate can be collected on a condensation surface that can be separated from the NCM 10 via an air gap or a vacuum, or can be discharged via a cold, inert sweep gas. In the latter two cases, condensation of vapor molecules takes place outside the membrane module. Theoretically, the type of driving force, together with the water-repelling nature of the membrane, permits full retention of non-volatile components, such as ions, macro-molecules and colloidal particles.

The manner in which the vapor pressure difference is generated across the membrane is determined by the specific module configuration. In the most commonly used configuration, direct contact membrane distillation (DCMD), the permeate-side consists of a condensation liquid (often clean water) that is in direct contact with the membrane.

The performance of the inventive membranes is described more in the following working examples. High permeate flux of greater than about 25 $L \cdot m^{-2} \cdot kg^{-1}$, greater than about 27 $L \cdot m^{-2} \cdot kg^{-1}$, or greater than about 30 $L \cdot m^{-2} \cdot kg^{-1}$ can be achieved including at a temperature of about 65° C. or about 75° C.

WORKING EXAMPLES

Additional embodiments are provided by the following non-limiting working examples and preparation methods.

PMO Nanoparticle Preparation

A template was prepared by adding a sodium hydroxide catalyst to an aqueous solution of cetyltrimethylammonium bromide (CTAB, surfactant template). A mixture of CTAB (250 mg, 6.86 10–1 mmol), distilled water (120 mL), and sodium hydroxide (875 µL, 2 M) was stirred at 80° C. during 50 minutes at 700 rpm in a 250 mL three neck round bottom flask. The resultant mixture was stirred for 1 h, then 600 µL of bis(triethoxysilyl)ethylene and 200 µL of pentafluorophenyl triethoxysilane were quickly added to the mixture to produce a sol-gel reaction, followed by stirring at 80° C. for 3 h. The mixture was then centrifuged during 20 minutes at 10 krpm, and the supernatants were removed.

After centrifugation, a solution of ammonium nitrate (6 $g \cdot L^{-1}$) was added to the mixture, which was then sonicated at 45° C. to remove the template.

Acetone was added to the mixture, followed by centrifugation at 10,000 rpm for 20 min. A supernatant was the removed from the mixture. This process was repeated three times. PMO nanoparticles were collected as a precipitant and then dried at room temperature for 24 hours.

Figure 2:
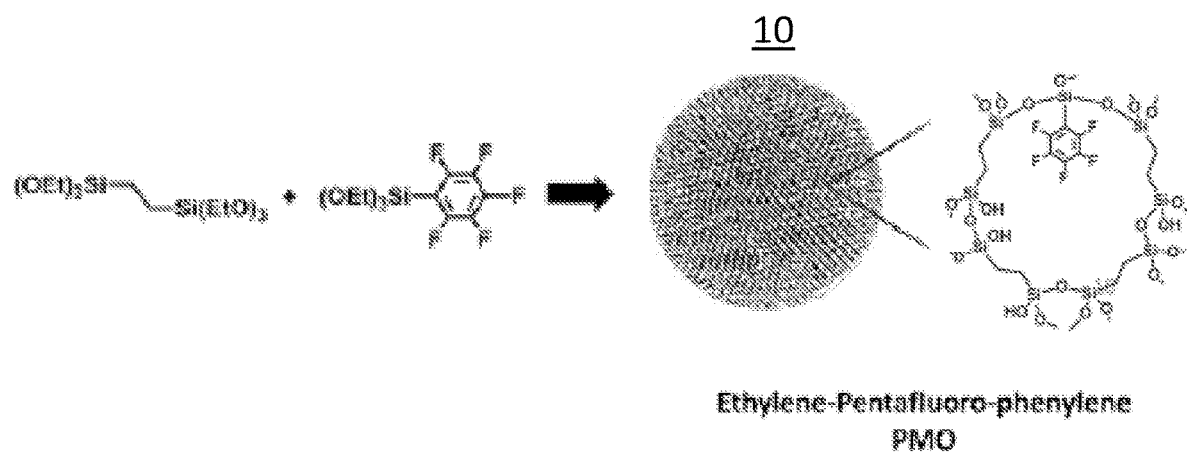
FIG. 2 is a schematic representation of formation of a PMO nanoparticle in one embodiment.
Figure 3A:
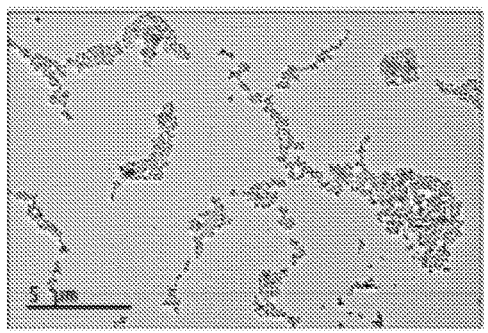
FIGS. 3A-3D are TEM micrographs of PMO nanoparticles for some embodiments.
Figure 3B:
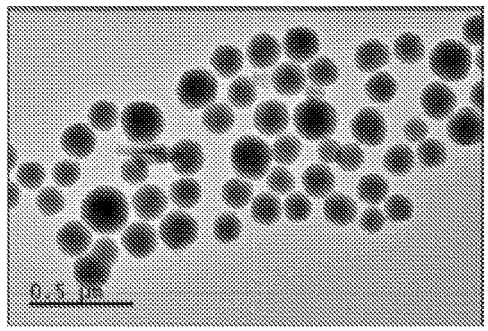
Figure 3C:
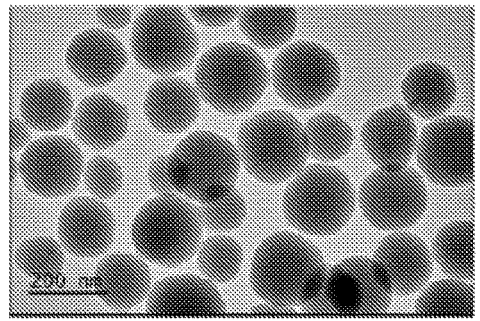
Figure 3D:
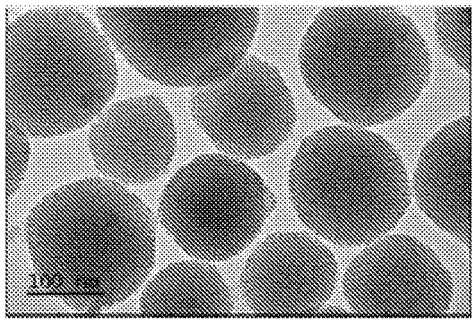

FIG. 2 is a schematic representation of a PMO nanoparticle 10, and FIGS. 3A-3D are transmission electron microsocpy (TEM) micrographs of PMO nanoparticles, according to various embodiments of the present disclosure. Referring to FIG. 2, the PMO nanoparticle 10 may be formed by reacting bis(triethoxysilyl)ethylene and pentafluorophenyl triethoxysilane in the presence of a template. The PMO nanoparticle 10 may include ethylene bridging groups and pentafluoro hydrophobic groups. Accordingly, the diversity in the chemical nature of the pore walls of the PMO nanoparticle 10 is theoretically unlimited.

Referring to FIGS. 3A-3D, the PMO nanoparticles were shown to be spherical particles have diameters ranging from about 100 to 200 nm. The PMO nanoparticles may have cubic pores, due to the ethylene-pentafluorophenylene bridging groups. However, the structures of the pores may be varied by varying the bridging groups. For example, varying the bridging groups may result in pores having three-dimensional hexagonal, two-dimensional hexagonal, and wormlike structures. When the ethylene silane is the only precursor, the pores can be cubic. When a mixture of silanes are used, the pores can be cubic or hexagonal or a mixture of both.

The nanoparticles were subjected to zeta potential measurement and found to have negative charge.

PEI/PMO Nanocomposite Fiber Membrane Preparation

Figure 4:
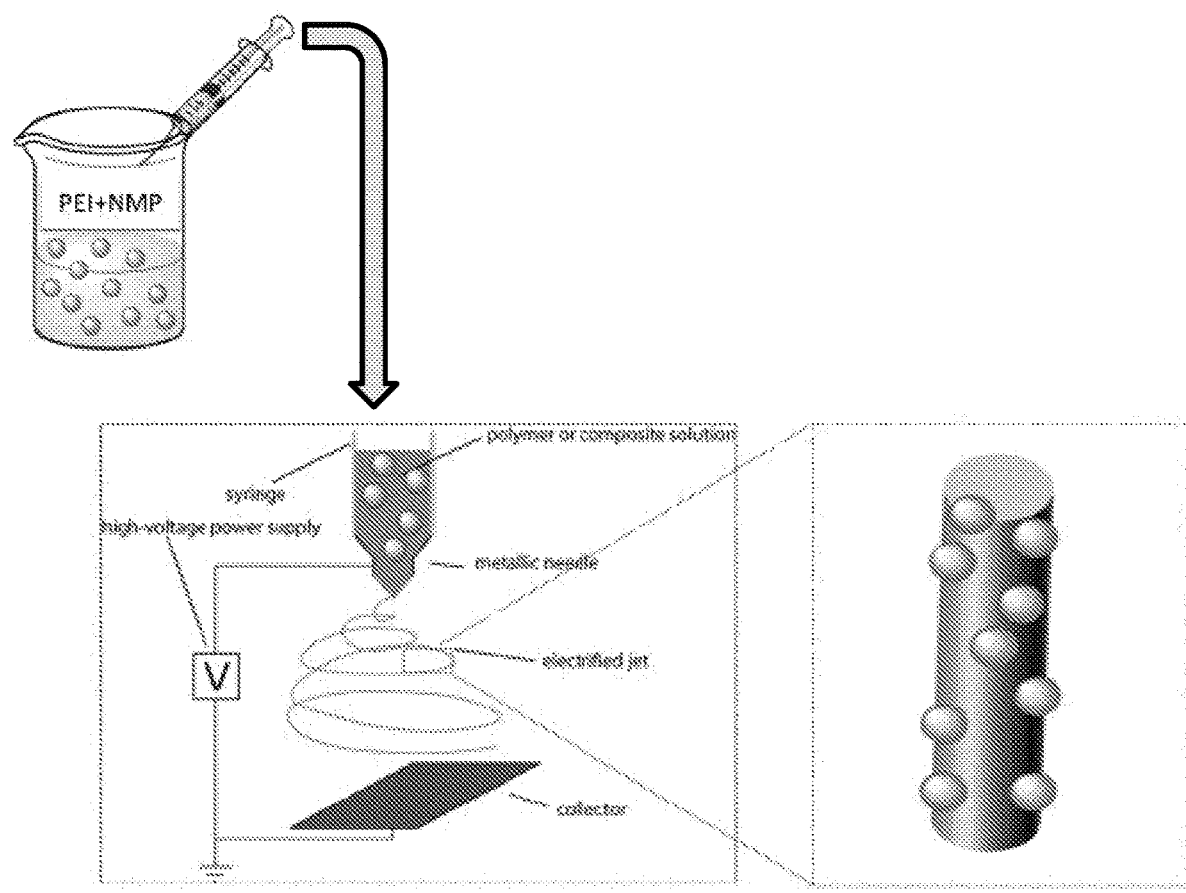
FIG. 4 illustrates a method of forming a nanocomposite membrane in one embodiment.

FIG. 4 illustrates a method of forming a PEI/PMO NCM according to various embodiments of the present disclosure. The structure of the PEI is shown below:

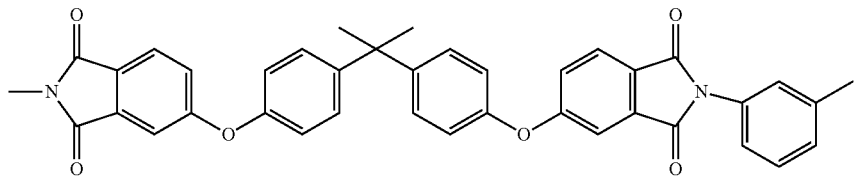

As-prepared PMO nanoparticles (5 or 10 wt %, $w_{NPs}$: $w_{PEI}$) were dispersed into N-methyl-2-pyrrolidone (NMP) followed by ultra-sonication. Then, PEI was added into the solution (17 to 20 wt %, $w_{PEI}$:$w_{NMP}$) and stirred at 50° C. for 24 h. The solution was electrospun using a 10 mL syringe with a 21 gauge needle, at a mass flow rate of 1 mL·h$^{-1}$. A high voltage (20 KV) was applied between the needle and a plate collector. The needle was moved in a zig-zag pattern above the plate collector using an automatic system to obtain a uniform membrane.

Figure 5A:
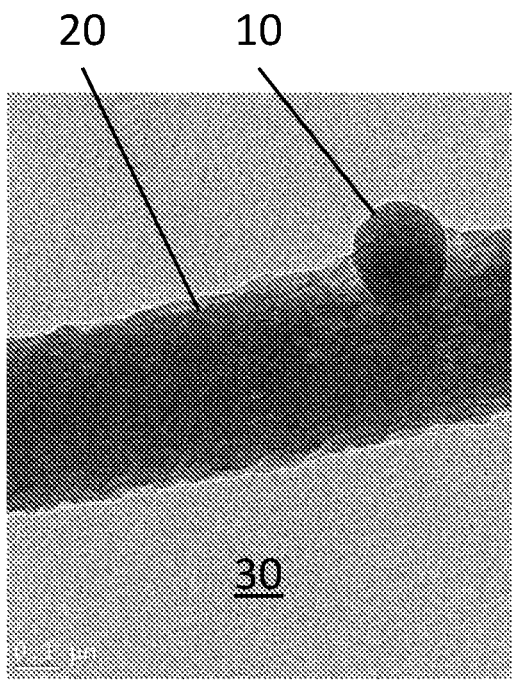
FIGS. 5A-5D are TEM micrographs (5A-B) and STEM micrographs (5C-D) showing PEI nanofibers doped with PMO nanoparticles in some embodiments.
Figure 5B:
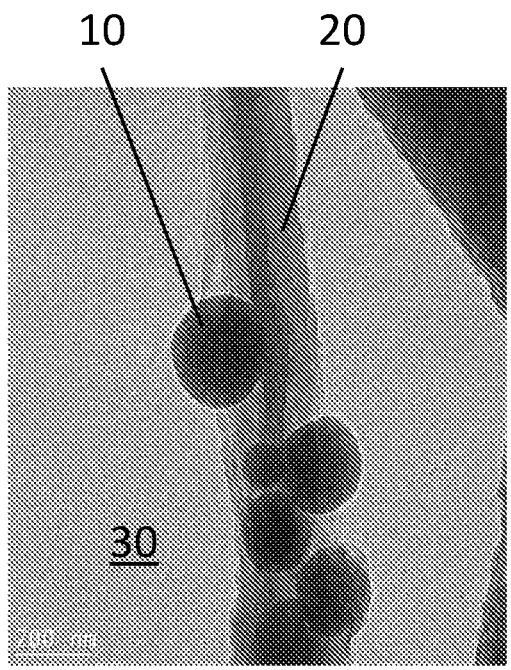
Figure 5C:
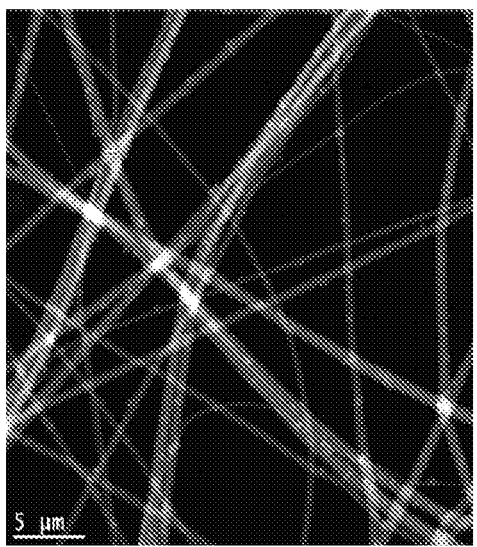
Figure 5D:
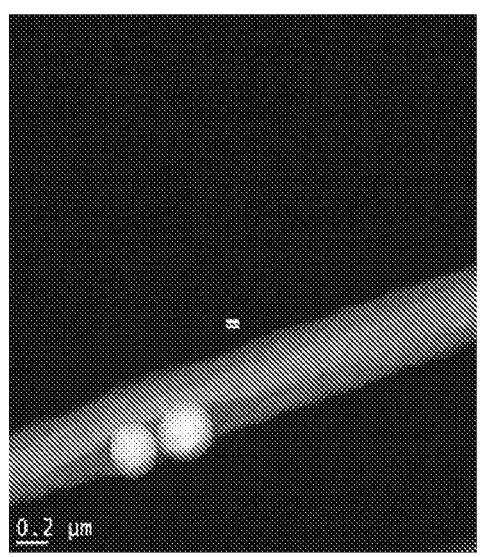
Figures 6A, 6B:
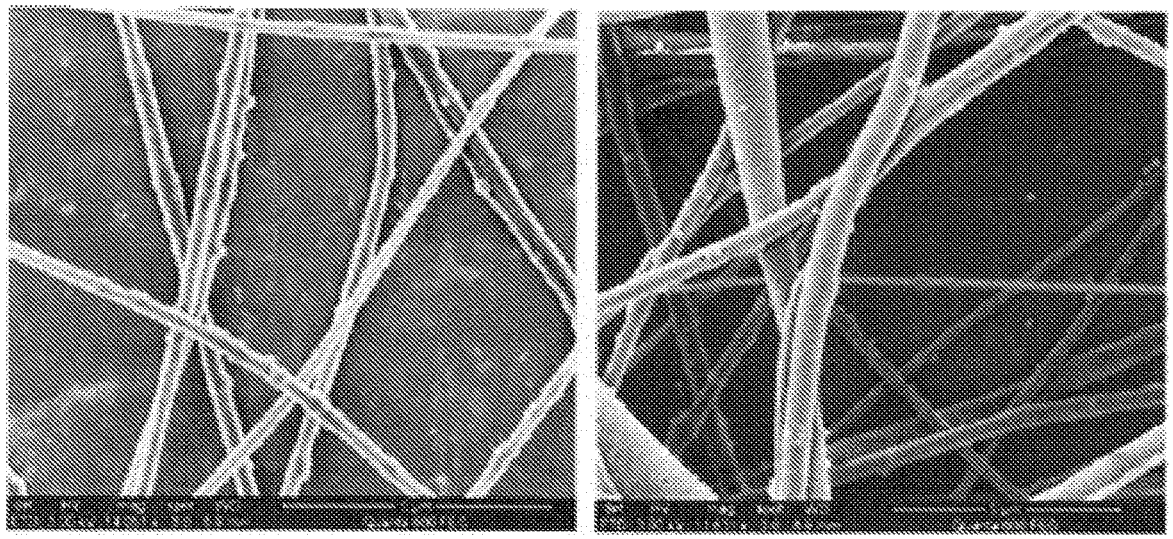
FIGS. 6A-6C are SEM micrographs showing PEI nanofibers doped with different concentrations of PMO nanoparticles in some embodiments.
Figure 6C:
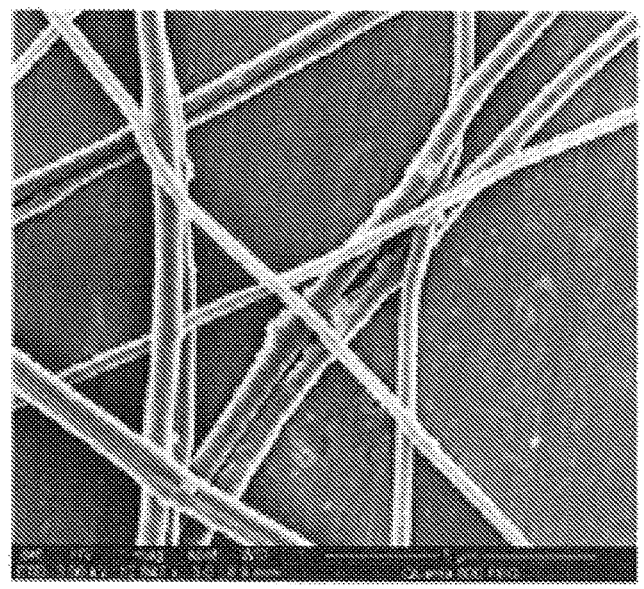

FIGS. 5A and 5B are TEM micrographs of PEI/PMO composite nanofibers 30. FIGS. 5C and 5D are scanning transmission electron microscopy (STEM) micrographs of the composite nanofibers 30. FIGS. 6A-6C are SEM micrographs of PEI/PMO composite nanofibers formed respectively from 20 wt %, 10 wt %, and 5 wt % PEI to solvent solutions.

Referring to FIGS. 5A-5D, the composite nanofibers 30 were shown to include PMO nanoparticles 10 that were generally uniformly dispersed along PEI nanofibers 20. However, some aggregation of PMO nanoparticles 10 was observed, as shown in FIG. 5B.

Referring to FIGS. 6A-6C, higher concentrations of PMO nanoparticles resulted in higher density deposition of PMO nanoparticle deposition on PEI nanofibers.

Figure 7:
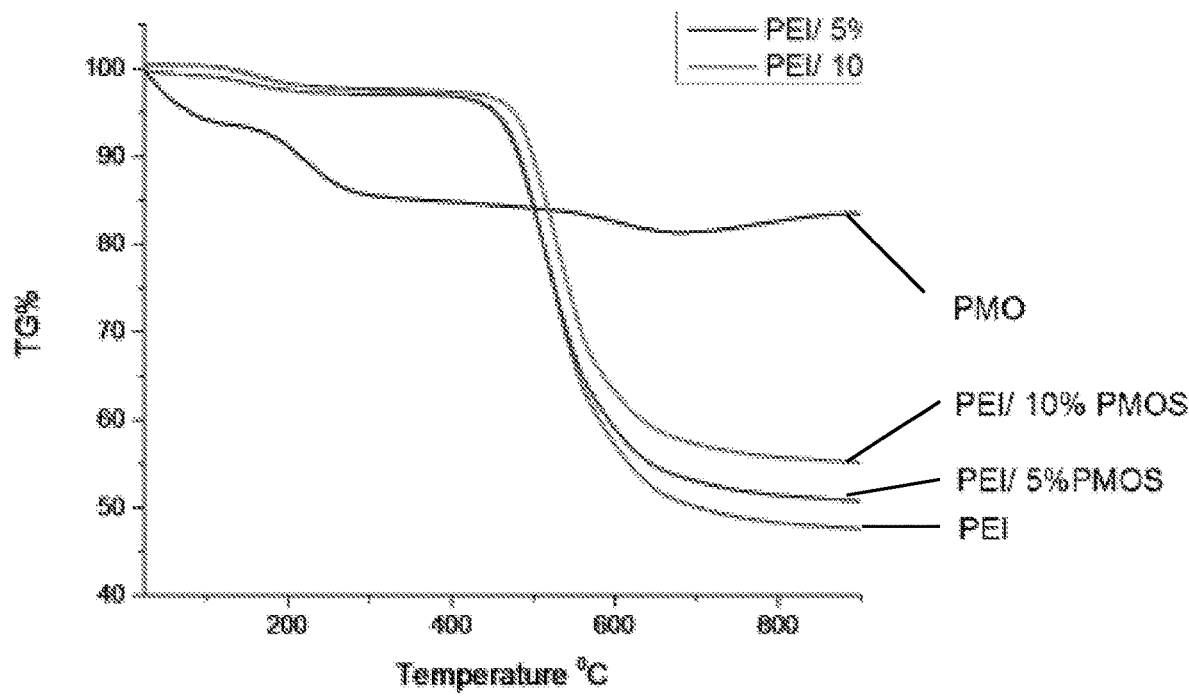
FIG. 7 is a graph showing mass loss with respect to temperature of nanocomposite membranes in some embodiments along with comparative membranes.

FIG. 7 is a graph illustrating weight loss of various membrane compositions. Referring to FIG. 7, thermo-gravimetric analysis studies were performed on PEI nanofibers, PMO nanoparticles, and PEI/PMO nanocomposite nanofibers. The results show that PMO nanoparticles do not significantly affect the thermal properties of the composite membranes including the same.

Figure 8:
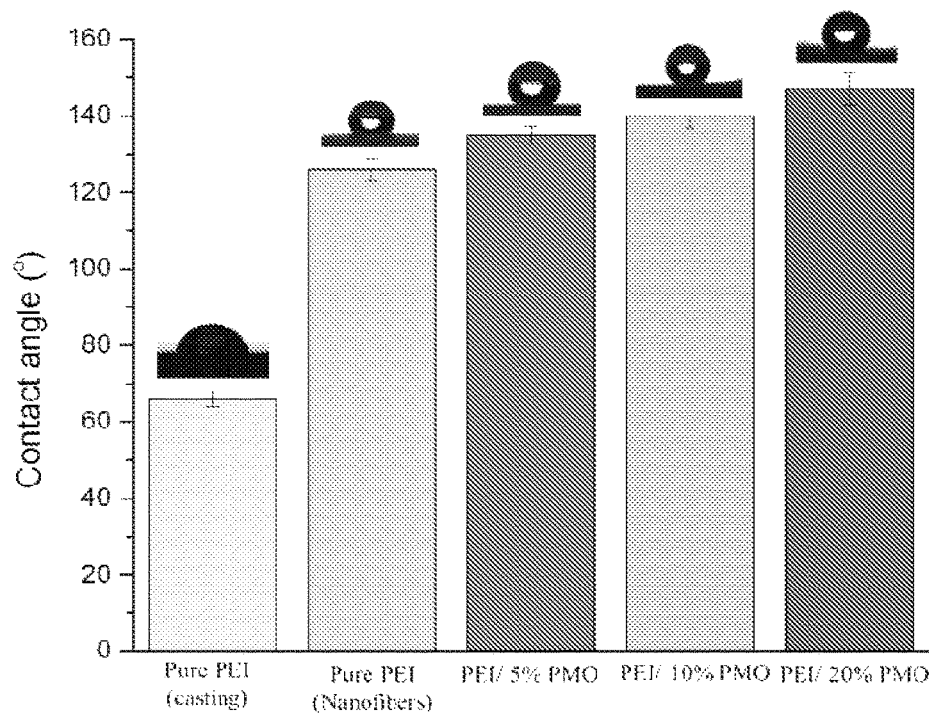
FIG. 8 is a graph showing water contact angles of nanocomposite membranes in some embodiments and comparative membranes.

FIG. 8 is a chart showing the hydrophobicities of a cast PEI membrane, an undoped electrospun PEI membrane, and electrospun membranes doped with various amounts of PMO nanoparticles, according to various embodiments of the present disclosure. Referring to FIG. 8, it can be seen that the electrospun membranes showed higher hydrophobicity than the cast PEI membrane, which is demonstrated by a contact angle increase from 64° to a minimum of 123° for the undoped electrospun membrane. The results also show a contact angle increase from 123° to 144° corresponding to increased amounts of PMO nanoparticle doping. In particular, the contact angle for the PMO nanoparticle-doped fibrous PEI membranes ranged from about 130° to about 144°, in accordance with increased PMO nanoparticle doping. This arose from the increase the hydrophobicity of the nanofiber membranes via the composition of PMO nanoparticles, via the low free-energy of fluorinated PMO. Note that, the change of surface roughness in the PEI/PMO membrane may have impacted the hydrophobicity as well, especially with regard to the difference between cast and fibrous membranes.

Table 1 shows the PEI concentration (%), thickness (microns), and PMO wt % of a commercial PTFE membrane (sample 0), PEI membranes (samples 1 to 4), and PEI/PMO composite membranes (samples 5 and 6).

TABLE 1

| Sample | PEI Concentration | Thicknesses | PMO % |
|---|---|---|---|
| 0 | Commercial membrane | | |
| 1 | 20 | 60 | 0 |
| 2 | 20 | 90 | 0 |
| 3 | 20 | 130 | 0 |
| 4 | 17 | 60 | 0 |
| 5 | 17 | 60 | 5 |
| 6 | 17 | 60 | 10 |

Figure 9:
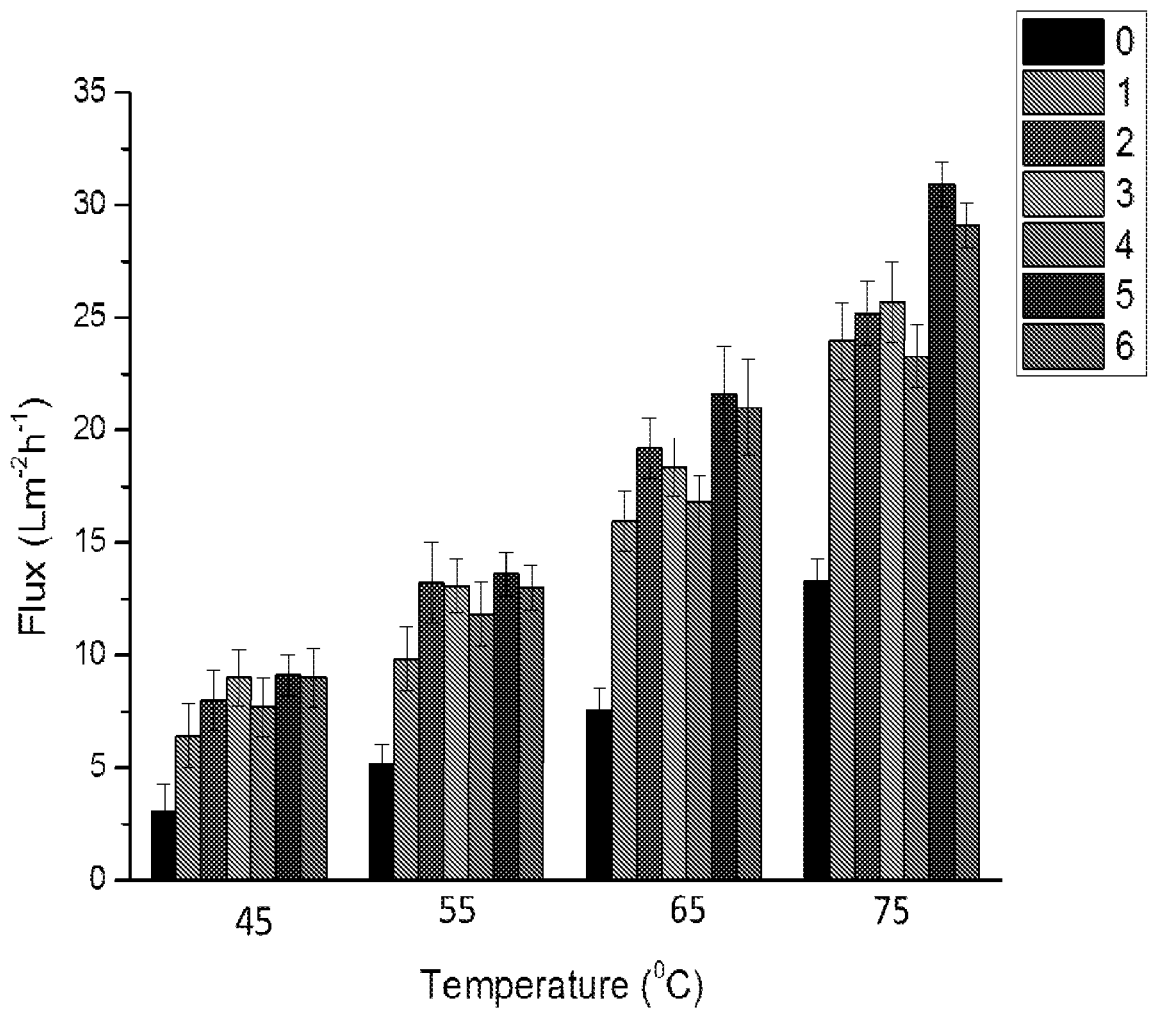
FIG. 9 is a graph showing the permeate flux of nanocomposite membranes in some embodiments and comparative membranes, at different temperatures.

FIG. 9 is a chart comparing the permeate flux of the sample membranes of Table 1, which were all tested for MD under the same operating conditions and at different temperatures. Referring to FIG. 9 and Table 1, it can be seen that permeate flux increased with the addition of PMO nanoparticles. This is particularly true for the temperatures of 65° C. and 65° C. Further, the membrane sample doped with 5% PMO nanoparticles generated the highest permeate flux of about 31 L·m$^{-2}$·kg$^{-1}$, which is significantly higher than the commercial membrane (13 L·m$^{-2}$·kg$^{-1}$). The color code in FIG. 9 is from left to right, for each temperature: 0 (black), 1 (red), 2 (light blue), 3 (pink), 4 (green), 5 (dark blue), and 6 (purple).

Figure 11:
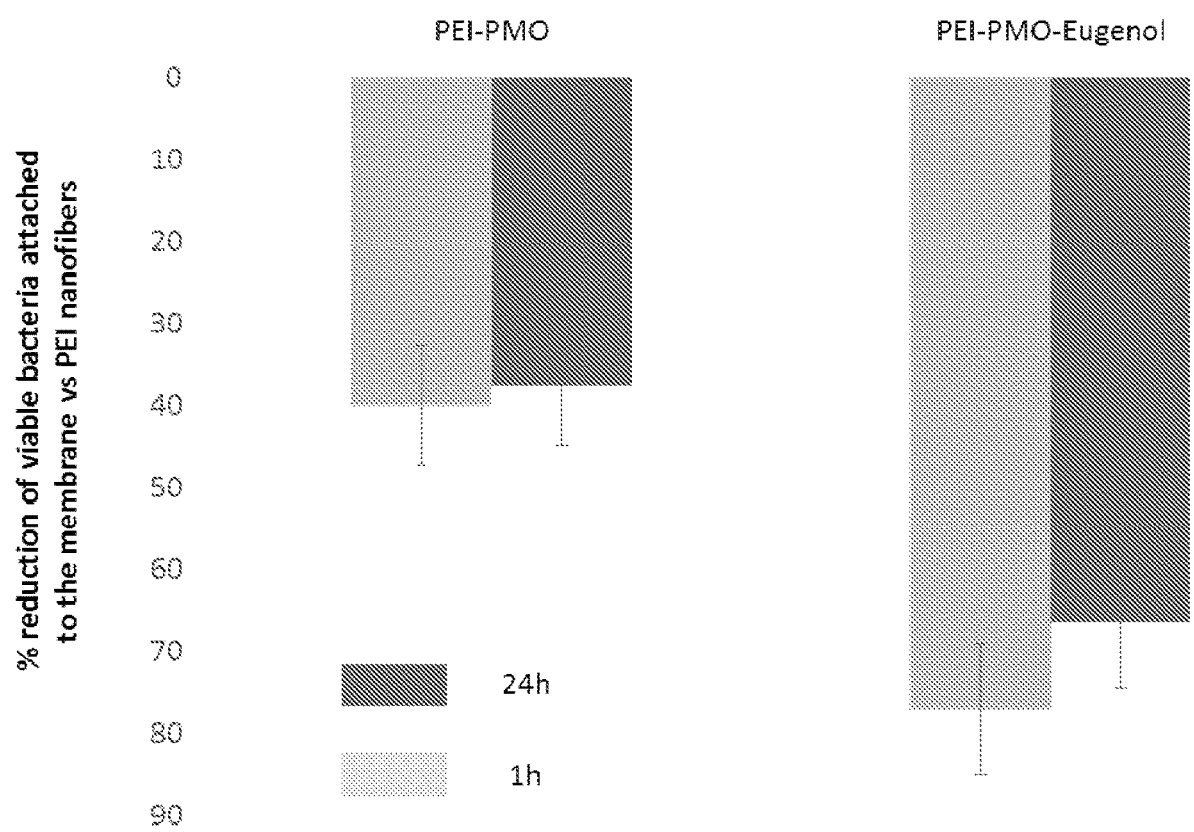
FIG. 11 illustrates reduction in bacterial attachment compared to the pristine PEI nanofiber.
Figure 12:
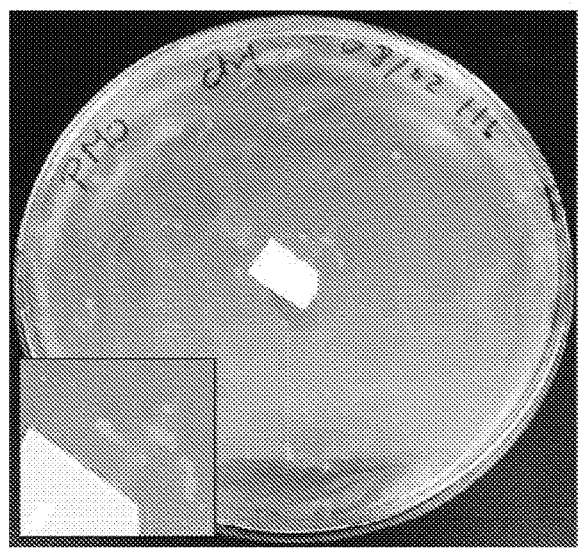
FIG. 12 illustrates the bacterial inhibition of the antimicrobial loaded PMO doped composite membrane.
Figure 12:
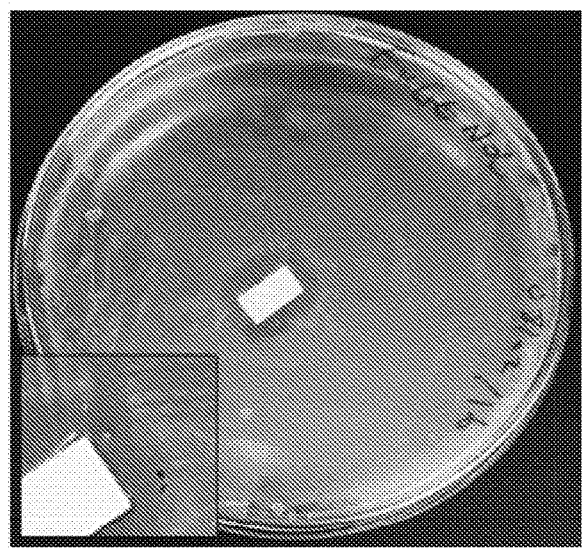

In addition, one can use the PMOs porosity to load anti-microbial molecule(s) to prevent biofilm on the membrane (FIGS. 11-12). Anti-microbial agents and related compounds such as anti-fungal agents and biocides are known in the art and can be metallic such as cuprous oxide, or can be organic, such as thymol, eugenol, guaiacol, or triclosan (5-chloro-2-(2,4-dichlorophenoxy)phenol). Mixtures of agents can be used. For example, a metallic agent can be used together with an organic agent.

Eugenol is an algaecide and antimicrobial molecule. The antibacterial activity of the antioxidant-loaded membrane was evaluated using ampicillin resistant E. coli to detect only the used bacteria. The bacterial growth can be visualized directly in a Petri dish. The inhibition zone were clearly observed after 24 h around the drug loaded nanofiber membrane, while the PEI/PMO nanocomposite did not show inhibition. The Eugenol and Triclosan loaded membrane inhibit bacterial growth in the area larger than the membrane itself because of the cargo diffusion into agar.

Furthermore, to evaluate the bacterial adhesion in the membrane the ampicillin resistant bacteria were used. PEI nanofiber, PEI/PMOs nanofibers and cargo-loaded PEI/PMOs nanofiber were soaked in the bacterial solution. The bacterial adhesion were significantly reduced by adding the F-PMOs. While the inventions are not limited by theory, this is likely due to the low surface energy of the F-PMOs nanoparticle and to the surface roughness of the composite nanofibers. Further improvement was observed by loading the antibacterial cargo to the PMOs nanoparticle due to the bacterial killing of the molecule.

According to various embodiments, provided are PMO nanoparticle functionalized NCM's that exhibit increased strength and durability, as compared to conventional membranes. The MCM's are environmentally friendly, cost effective, and may be highly hydrophobic. In addition, the characteristics of the NCM's, such as hydrophobicity, flux, and biofouling time, may be tuned by controlling the concentration of the PMO nanoparticles.

LISTING OF REFERENCES

The following references (which are not admitted prior art) provide additional background and contribute to enabling disclosure in the present application including methods of making membranes, methods of using membranes, and methods of characterizing membranes.
1. Prince, J., et al., Nanofiber based triple layer hydrophilic/-phobic membrane—a solution for pore wetting in membrane distillation. *Scientific reports* 2014, 4.
2. Ghaffour, N., et al., Technical review and evaluation of the economics of water desalination: current and future challenges for better water supply sustainability. *Desalination* 2013, 309, 197-207.
3. Organization, W. H., "Progress on Drinking-Water and Sanitation—2012 Update" launched on 6 Mar. 2012. 2012.
4. Francis, L., et al., PVDF hollow fiber and nanofiber membranes for fresh water reclamation using membrane distillation. *Journal of Materials Science* 2014, 49 (5), 2045-2053.
5. Tijing, L. D., et al., Recent progress of membrane distillation using electrospun nanofibrous membrane. *Journal of Membrane Science* 2014, 453, 435-462.
6. Francis, L., et al., Fabrication of electrospun nanofibrous membranes for membrane distillation application. *Desalination and Water Treatment* 2013, 51 (7-9), 1337-1343.
7. Ho, C.-D., et al., Theoretical and experimental studies of flux enhancement with roughened surface in direct contact membrane distillation desalination. *Journal of Membrane Science* 2013, 433 (0), 160-166.
8. Dong, Z.-Q., et al., Superhydrophobic modification of PVDF-SiO2 electrospun nanofiber membranes for vacuum membrane distillation. *RSC Advances* 2015.
9. Ma, M., et al., Decorated electrospun fibers exhibiting superhydrophobicity. *Advanced Materials* 2007, 19 (2), 255-259.
10. Guo, F., et al., Desalination by Membrane Distillation using Electrospun Polyamide Fiber Membranes with Surface Fluorination by Chemical Vapor Deposition. *ACS applied materials & interfaces* 2015, 7 (15), 8225-8232.
11. Khayet, S. M., et al. Nanostructured flat membranes for direct contact membrane distillation. WO 2011/117,443.
12. Nunes, S. P., et al., Polyazole membrane for water purification. EP 2626127.
13. Nunes, S. P. et al., Membrane for water purification. US Patent Publication 2013/0206694.
14. Wang, P., et al., Recent advances in membrane distillation processes: Membrane development, configuration design and application exploring. *Journal of Membrane Science* 2015, 474, 39-56.
15. Tijing, L. D., et al., A novel dual-layer bicomponent electrospun nanofibrous membrane for desalination by direct contact membrane distillation. *Chemical Engineering Journal* 2014, 256, 155-159.
16. Cath, T. Y. et al., Combined membrane-distillation-forward-osmosis systems and methods of use. U.S. Pat. No. 8,029,671.

What is claimed is:

1. A nanocomposite membrane (NCM) for membrane distillation, the NCM comprising:
  polymer fibers aggregated into a matrix; and
  periodic mesoporous organosilica (PMO) nanoparticles disposed on the polymer fibers, the PMO nanoparticles comprising hydrophobic functional groups comprising pentafluorinated organic groups.

2. The NCM of claim 1, wherein the fluorinated organic groups comprise pentafluorophenyl groups.

3. The NCM of claim 2, wherein the pentafluorophenyl groups are covalently bonded to silicon atoms of the PMO nanoparticles.

4. The NCM of claim 1, wherein the PMO nanoparticles comprise —$CH_2$— bivalent groups.

5. The NCM of claim 1, wherein the polymer fibers comprise polyetherimide (PEI), poly vinylidene fluoride (PVDF), poly(methyl methacrylate) (PMMA), polysulfone, or any combination thereof.

6. The NCM of claim 1, wherein the polymer fibers comprise polyetherimide (PEI).

7. The NCM of claim 1, wherein the PMO nanoparticles are spherical particles having an average diameter of from 50 nm to 500 nm.

8. A method of forming the NCM of claim 1, the method comprising a step of electrospinning a polymer composition comprising the PMO nanoparticles comprising pentafluorinated organic groups.

9. A nanocomposite membrane (NCM) for membrane distillation, the NCM comprising:
  polyetherimide (PEI) fibers aggregated into a matrix; and
  periodic mesoporous organosilica (PMO) nanoparticles disposed on the PEI fibers, the PMO nanoparticles comprising hydrophobic functional groups comprising pentafluorinated organic groups.

10. The NCM of claim 9, wherein the PEI fibers having a fiber diameter is ranging from about 200 to about 600 nm.

11. The NCM of claim 9, wherein the PMO nanoparticles are spherical particles having an average diameter of from 50 nm to 500 nm.

* * * * *